United States Patent [19]
Hager et al.

[11] Patent Number: 6,090,070
[45] Date of Patent: *Jul. 18, 2000

[54] DEVICE FOR ADMINISTERING METERED AMOUNTS OF A LIQUID MEDICAMENT

[75] Inventors: Jörg-Christian Hager; Kurt Gebhart, both of Cologne; Helmut Löwenich, Jüchen; Ulrich Pastewka, Bonn, all of Germany

[73] Assignee: Rhone-Poulenc Rorer GmbH, Cologne, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/799,018

[22] Filed: Feb. 10, 1997

[51] Int. Cl.⁷ .......................... A61M 37/00; A61M 5/178; A61M 5/32; A61M 5/00
[52] U.S. Cl. .......................... 604/131; 604/207; 604/186; 604/196
[58] Field of Search .................................... 604/131, 134, 604/136, 139, 143, 146, 154, 156, 157, 186, 191, 201, 207, 213, 232, 71, 195, 196

[56] References Cited

U.S. PATENT DOCUMENTS

| Re. 25,113 | 1/1962 | Wilburn . |
| 3,058,584 | 10/1962 | Marshall . |
| 3,353,537 | 11/1967 | Knox et al. . |
| 3,461,867 | 8/1969 | Zimmet et al. ............................ 604/71 |
| 3,527,216 | 9/1970 | Snyder .................................... 604/196 |
| 3,572,556 | 3/1971 | Pogacar . |
| 3,677,246 | 7/1972 | Stein . |
| 4,064,879 | 12/1977 | Leibinsohn ............................... 604/218 |
| 4,128,173 | 12/1978 | Lazarus et al. . |
| 4,184,593 | 1/1980 | Dorr . |
| 4,301,795 | 11/1981 | Zimmermann .......................... 604/143 |
| 4,351,335 | 9/1982 | Whitney et al. . |
| 4,643,723 | 2/1987 | Smit ....................................... 604/207 |
| 4,657,138 | 4/1987 | Watson . |
| 5,049,125 | 9/1991 | Accaries et al. ........................... 604/71 |
| 5,080,648 | 1/1992 | D'Antonio ................................ 604/71 |
| 5,092,842 | 3/1992 | Bechtold et al. ....................... 604/135 |
| 5,114,406 | 5/1992 | Gabriel et al. .......................... 604/136 |
| 5,256,142 | 10/1993 | Colavecchio .............................. 604/71 |
| 5,358,489 | 10/1994 | Wyriuck . |
| 5,380,279 | 1/1995 | Schmidt .................................. 604/143 |
| 5,779,678 | 7/1998 | Carter . |

FOREIGN PATENT DOCUMENTS

| 0 397 607 | 11/1990 | European Pat. Off. . |
| 0723784 | 7/1996 | European Pat. Off. . |
| 2 721 498 | 12/1995 | France . |
| 14 91 841 | 7/1969 | Germany . |
| 74 16 784 | 5/1974 | Germany . |
| 85 30 363 | 1/1986 | Germany . |
| 37 08 857 | 9/1988 | Germany . |
| 43 01 282 | 7/1994 | Germany . |
| 195 21 016 | 12/1996 | Germany . |
| 195 32 410 | 3/1997 | Germany . |
| 196 48 326 | 6/1997 | Germany . |
| 196 04 838 | 8/1997 | Germany . |
| 227895 | 3/1991 | New Zealand . |
| 2187962 | 9/1987 | United Kingdom . |
| WO 94/24021 | 10/1994 | WIPO . |
| WO 96/25966 | 8/1996 | WIPO . |

*Primary Examiner*—Sharon Kennedy
*Attorney, Agent, or Firm*—Proskauer Rose LLP

[57] ABSTRACT

A sale unit for the parenteral application of liquid pharmaceutical products by the user is described, whereby the unit comprises at least one cannula, a device to emit a given liquid amount of the pharmaceutical product in single doses, as well as at least one vessel filled with the pharmaceutical product, the vessel being arranged within the device and emptied in single doses by means of the device, and whereby each single dose corresponds to the given liquid amount of the pharmaceutical product.

24 Claims, 10 Drawing Sheets

FIG. I

DEVICE FOR ADMINISTERING METERED AMOUNTS OF A LIQUID MEDICAMENT

BACKGROUND OF THE INVENTION

The present invention is directed to a sale unit for the parenteral application of liquid pharmaceutical products, to a device for carrying out this parenteral application and to a refill unit for the afore mentioned sale unit, respectively device.

Parenterally applicable liquid pharmaceutical products, meaning such products that are subcutaneously applied by means of a syringe, nowadays are applied mainly by correspondingly trained professional staff, as for example by doctors or nursing staff. Hereby a usual syringe is used which is filled with the corresponding liquid pharmaceutical product before the parenteral application or which is filled already as a one-way syringe with the liquid pharmaceutical product. However, this means that the respective user has to submit himself to a medical treatment which involves high expenses particularly when, for the therapy of the respective disease, a given amount of a liquid pharmaceutical product has to be injected subcutaneously each day for a given limited time period.

The present invention has the object of elaborating a possibility by which the respective user can parenterally and preferably subcutaneously apply a liquid pharmaceutical product particularly easily.

SUMMARY OF THE INVENTION

According to the invention, this object is realized by a sale unit for the parenteral application of a liquid pharmaceutical product by the user for the required therapy period is based on the main thought that the user can dispose, during the medically prescribed treatment period, of all necessary parts, so that the user is able to parenterally and preferably subcutaneously apply himself the required liquid pharmaceutical product without the help of medical staff. For that reason, the inventive sale unit comprises at least one cannula, one device for emitting a given liquid amount of the pharmaceutical product in single doses, as well as at least one vessel filled with the liquid pharmaceutical product, whereby the vessel can be set in the device and emptied by means of the device and whereby each single dose corresponds-to the given liquid amount of the pharmaceutical product. In other words, the user only needs to provide the device for emitting a given liquid amount, the device being arranged within the unit, with a cannula also arranged within the unit and, furthermore, to put the vessel filled with the liquid pharmaceutical product in the emitting device, so that immediately hereafter the user can parenterally and preferably subcutaneously apply himself the single dose of the liquid pharmaceutical product prescribed by the doctor.

The inventive sale unit has a range of advantages. Conditioned by the fact that the inventive sale unit comprises all parts that the user needs and that are required for the parenteral application in a single sale unit, it is firstly to be noted that, on one hand, these parts can be commonly stored in the sale unit by the user himself during the treatment and that, on the other hand, it is made particularly easy for the prescribing doctor to prescribe this sale unit as a whole. Since the emitting device of the sale unit forcibly determines, as a result of its construction, the given amount of the liquid pharmaceutical product for each single dose, the liquid pharmaceutical product cannot be underdosed or overdosed in the inventive sale unit, so that hereby the parenteral application of the liquid pharmaceutical product by the user is particularly safe. Moreover, the user can dispose of the parts required for the parenteral application in a well and clearly-arranged way, whereby the acceptance of the inventive sale unit is essentially improved for the user. Furthermore, the inventive sale unit avoids a soiling of its parts, particularly during their use for the user, and makes the expedition and the storing easier since it is formed as a unit, which is particularly advantageous for the use in the trade.

A first embodiment of the inventive sale unit is characterized in that the unit comprises a number of cannulas that corresponds to a number of the single doses of the pharmaceutical product. Hereby the user can exchange the used cannula by a corresponding sterile cannula after each parenteral application of the liquid pharmaceutical product, whereby the risk of an infection is avoided. The cannulas provided in the sale unit are preferably constructed in that way that the actual needle of the cannula is protected by a solid plastic jacket, whereby this solid plastic jacket, on one hand, guarantees the sterility of the needle and, on the other hand, keeps the user from unintentionally hurting himself with the needle. Such an embodiment of the sale unit particularly comprises ten of the afore described cannulas, whereby then the vessel being provided in the sale unit and being filled with the liquid pharmaceutical product makes it possible to correspondingly apply ten single doses of the product to be parenterally applied.

In order to make it again easier for the user to operate the inventive sale unit during the parenteral application, a further advantageous development is directed to a sale unit that comprises a number of cannulas that corresponds to a number of sponges, whereby these sponges are moistened with a disinfectant, as for example a low alcohol, ethanol, propanol. In order to avoid on the sponges an undesired evaporation of the disinfectant, the sponges moistened with a disinfectant are wrapped singly in corresponding foils, preferably plastic foils and more preferably compound plastic foils, so that, for the parenteral application, the user removes just one sponge from the wrapping and disinfects herewith the spot chosen for the injection.

In another embodiment of the inventive sale unit, the unit additionally comprises a section serving to take up the used cannulas and/or used sponges. Hereby this section to take up the used cannulas, respectively the used sponges, and is formed in the way that the used cannulas, respectively sponges, cannot fall out of the sale unit while being used, so that the section is formed particularly as a separately closable section. If in the sale unit this section is formed as a section being detachable from the sale unit, as for example as a closable box, the used cannulas and, if necessary, the sponges can be separately wasted, as for example by the special trade, as far as this is required by legal prescriptions.

The inventive sale unit can comprise basically each vessel containing the multitude of single doses of the liquid pharmaceutical product, as far as it is guaranteed that this vessel is formed in that way that it can be set into the device and emptied in single doses by means of the device. However, it is particularly suitable to fill the liquid pharmaceutical product to be parenterally applied by the user in single doses in a cylindrical or cylinder-like glass carpule (glass syringe cylinder), whereby such a glass carpule holds particularly between about 1.5 ml and about 8 ml, preferably between about 2 ml and about 6 ml, of the liquid pharmaceutical product.

A particularly advantageous development of the afore described glass carpule is characterized in that in the inventive sale unit such a glass carpule is arranged which is closed, at its bottom side, by a piercable membrane and, at its top side, by a plug being formed in that way that it can be axially shifted within the glass carpule in the direction of the piercable membrane when the liquid level is descending. This special development of the glass carpule has the particular advantage that the bottom section of the plug is located in the immediate proximity of the liquid level or even contacts the liquid level, so that there is no air puffer above the respective liquid level when the liquid level is descending because of the single doses emitted. On one hand, this avoids an undesired oxidative modification of the respective liquid pharmaceutical product and, on the other hand, the special forming of the plug effectively avoids the formation of a vacuum in the glass carpule when the liquid amount is decreasing, whereby such a vacuum would have a negative effect on the exactness of the liquid amount emitted in single doses.

In order to ensure the required tightness between the plug and the inner walling of the glass carpule, according to the afore described embodiment of the glass carpule which disposes of the afore described plug being axially shiftable in the direction of the piercable membrane, a further development of the inventive sale unit is characterized in that the plug comprises on its jacket surface at least one, preferably two to five, disk-like sections directing radially to the outside. Hereby these disk-like sections can be deformed when the plug is inserted into the glass carpule with the formation of a sealing surface which liquid-tightens and air-tightens the inner surface of the carpule. The disk-like sections directing to the outside are preferably dimensioned in that way that an end section of the disk-like sections is elastically deformed by the axial shifting of the plug in the glass carpule opposite to the shifting direction with the formation of a correspondingly larger dimensioned sealing surface. In respect to the material that the plug consists of, it is to be noted that herefore preferably an elastic, chemically resistant plastic material or rubber material is chosen, whereby herefore a halogenbutyl-rubber proved to be particularly suitable.

When the afore described plug can be axially shifted within the glass carpule by a power of less than 10 N, preferably by a power of between 4 N and 8 N, it is particularly guaranteed that the above described advantages occur in a particularly reproducible way.

By using the inventive sale unit, basically all liquid pharmaceutical products being stable in storage can be parenterally applied by the user himself. Hereby the term liquid pharmaceutical products means all such products which, as actual product, are liquid or from which stable solutions, stable dispersions or stable emulsions can be manufactured in an organic or inorganic, physiologically safe liquid. The afore described vessel or the afore described and particularly used glass carpule preferably comprise an aqueous solution of a heparin, preferably an aqueous solution of a low-molecular heparin, and particularly an aqueous solution of an enoxaparin-sodium. Such a sale unit is then used by such users who, because of their syndrome and from the medical point of view, have to apply the heparin daily in constant single doses for a longer time period, in order to prevent, for example, the risk of a thrombosis after having discharged the patient from the hospital. A further preferred employment of the inventive sale unit is the regular parenteral application of a given and constant amount of a growth hormone, whereby, for this case of application, the vessel and particularly the afore described glass carpule is filled with a solution of the growth hormone, preferably an aqueous solution of the growth hormone. Within the scope of the present invention, the term water does not only mean deionized or distilled water, but all aqueous systems, particularly physiological salt solutions or buffer solutions.

The present invention is furthermore directed to a device for emitting a given liquid amount of a pharmaceutical product in single doses, whereby the inventive device comprises a section arranged within a casing, the section taking up the vessel filled with the liquid pharmaceutical product. Moreover, the inventive device contains an outlet section for the single dose of the pharmaceutical product, whereby the outlet section directs into the direction of the user when he parenterally and particularly subcutaneously applies the single dose of the pharmaceutical product. According to the inventive device, the vessel containing the multitude of single doses, can be connected with the outlet section by an intermediate reservoir in such a way that, when the vessel is set into the inventive device, the given liquid amount of each single dose can be drained firstly from the vessel into the intermediate reservoir and then from the intermediate reservoir into the outlet section. The amount of the liquid pharmaceutical product emitted with each single dose can be determined, according to the inventive device, by the volume of the intermediate reservoir. In other words, the amount of the single dose being parenterally applicable is variable in the inventive device by varying the volume of the intermediate reservoir, whereby the volume of the intermediate reservoir is chosen in that way that each single dose of the liquid pharmaceutical product to be applied has a volume of between 0.1 ml and 1 ml, particularly between 0.2 ml and 0.6 ml and preferably between 0.2 ml and 0.4 ml.

The inventive device shows a number of advantages. First of all it is to be noted that it has a relatively simple and unproblematical construction and that it is very easy to handle since for the use of the inventive device by the user, it is only necessary to arrange the vessel containing the multitude of single doses of the liquid pharmaceutical product within the section for taking up the vessel located in the inventive device and to fix it there, if necessary, so that subsequently within the inventive device the vessel is connected with the intermediate reservoir which is then connected with the outlet section. In other words, when the respective user, contrarily to the initially described procedure of parenterally applying a liquid pharmaceutical product by a doctor or the medical staff, uses the inventive device, he does not have to transmit the respective product to be applied from the ampoule into the syringe and to measure the exact amount to be injected since in the inventive device this procedure takes places inevitably because of the construction of the inventive device. This essentially simplifies the use of the inventive device, so that by using the inventive device even sick and/or old users are able to inject themselves the required single dose of the product to be parenterally applied without depending on the help of others.

In order to form in the inventive device the afore mentioned connection between the vessel being set into the device and the intermediate reservoir in a particularly simple way, a further development of the inventive device is characterized in that at least one connecting conduit is located between the set in vessel filled with the multitude of the single doses of the liquid pharmaceutical product and the intermediate reservoir. Hereby an end section of this connecting conduct preferably protrudes into the section being arranged within the casing of the inventive device and taking up the vessel filled with the pharmaceutical product, so that, when the vessel has to be put in, this end section simplifies the connecting of the intermediate reservoir and the set in vessel. If hereby the glass carpule, which is described above in connection with the inventive sale unit and which comprises particularly at its top end the afore mentioned piercable membrane, is used as a vessel, it is suitable to form this end section of the connecting conduct as a correspondingly pointed end section or preferably as hollow needle, so that by this pointed end section, respectively by this hollow needle, then the piercable membrane can be pierced and so that thus the afore mentioned connection between the content of the glass carpule and the intermediate reservoir can particularly easily be realized. Such a piercing of the piercable membrane can also be simplified by providing the pointed end section, respectively the hollow needle, with a stopping element for the carpule, whereby this stopping element preferably fixes the carpule shaft and thus the whole carpule in its position. If hereby this stopping section is formed as a thread or as a bayonet catch, meaning that the thread, respectively the bayonet catch, can receive the correspondingly formed section of the carpule shaft, the carpule forcibly moves axially in the direction of the connecting conduct when the carpule is screwed in, respectively fixed, so that hereby the end section formed as pointed end section, respectively as hollow needle, penetrates the piercable membrane and so that thus the liquid pharmaceutical product can flow from the glass carpule into the intermediate reservoir.

A further development of the afore described embodiment of the inventive device is characterized in that the connecting conduct comprises a valve avoiding a backflow of the liquid from the intermediate reservoir into the glass carpule. In other words, this embodiment of the inventive device thus comprises a connecting conduct being provided with a reflux valve, so that the liquid to be parenterally applied can superfuse the connecting conduct only in one single direction, meaning from the vessel into the intermediate reservoir.

In respect to the formation of the afore mentioned valve avoids a backflow of the liquid pharmaceutical product from the intermediate reservoir into the vessel, as this is already described above, there are several possibilities. This upper section can be formed, for example, as a usual ball-containing reflux valve. However, it is particularly suitable when the reflux valve is formed as a membrane valve, whereby a valve sheet, preferably consisting of a rubber-elastic material, can be moved between a first position in which the valve sheet covers the partial conduct section of the connecting conduct, whereby the partial conduct section is directed to the vessel, and between a second position in which the valve sheet is displaced in the direction of the intermediate reservoir and makes possible the liquid flow from the vessel into the intermediate reservoir. In order to prevent an adhesion of the disk-shaped valve sheet in the first position and to avoid thus a disturbance of the functioning of the reflux valve, it is suitable to provide a ring-shaped distancing element which gets in contact with the valve sheet when the valve sheet is in the first position, so that in all the sealing surface is decreased by the ring-shaped distancing element, as this is subsequently described in detail in a example.

For filling the intermediate reservoir in the inventive device with the single dose of the liquid pharmaceutical product from the vessel, the content of the vessel can flow into the intermediate reservoir and thus fill it for gravitation reasons. It is particularly suitable, however, when a piston being axially shiftable in the direction of the outlet section is arranged within the intermediate reservoir, whereby, with such an axial shifting in the direction of the outlet section, the piston then effectuates the flow of a single dose of the liquid pharmaceutical product, the single dose being located in the intermediate reservoir, in the direction of the outlet section. According to an axial shifting in the opposite direction hereof, a vacuum is generated in the intermediate reservoir if the connection between the intermediate reservoir and the outlet section is closed air-tight, so that a connecting conduct extending through the piston, the connecting conduct being located between the vessel and the intermediate reservoir, fills the intermediate reservoir with the liquid from the vessel filled with the liquid pharmaceutical product. Such a filling of the intermediate reservoir has the particular advantage that hereby a reproducibly and exactly given liquid amount drains from the vessel into the intermediate reservoir, so that correspondingly the single dose of the liquid pharmaceutical product from the intermediate reservoir which is applied by the user can be formed in a particularly exact and reproducible way.

In order to obtain in the inventive device the air-tight blocking which is required before for the filling and which blocks the conduct located between the intermediate reservoir and the outlet section, there are several possibilities. For example, a valve, particularly a reflux valve, can be arranged also in this conduct, whereby this valve does not allow an air flow or a liquid flow from the outlet section into the intermediate reservoir, but only a liquid flow from the intermediate reservoir into the outlet section. It is particularly suitable, however, when the conduct comprises a closing element being operable from the outside, as for example a corresponding valve.

An embodiment of the inventive device which is particularly easy to handle by the respective user for a long time period is characterized in that the already afore mentioned closing element by which the conduct connecting the outlet section with the intermediate reservoir can be closed air-tight is formed as detachable closing element being located at the conduct. Hereby a sealing section of the closing element air-tightens the outer conduct outlet located at the outlet section. This closing element is preferably formed as a closing element which can be screwed onto the device in the outlet section or which can be fixed by a bayonet catch in such a way that it is detachably connectable with the outlet section and/or the casing of the device. If in this embodiment of the inventive device it is desired to fill the intermediate reservoir with the single dose of the liquid pharmaceutical product in the afore described manner, which means that an air flow from the conduct outlet of the outlet section into the intermediate reservoir is avoided and that thus the vacuum required for the filling of the intermediate reservoir is generated, this closing element is screwed onto the outlet section, respectively onto the corresponding zone of the casing, so that the sealing section located at the closing element gears in with the conduct outlet. After filling the intermediate reservoir, the closing element is detached from the outlet section, respectively from the zone of the device casing, so that the single dose of the liquid pharmaceutical product, the single dose being located in the intermediate reservoir, can be drained out of the inventive device by axially shifting the piston in the direction of the outlet section and the consequently opened conduct.

A particularly high reproducibility in respect to the liquid pharmaceutical product amount emitted with each single dose can be obtained in such an embodiment of the inventive device, when it is guaranteed that the intermediate reservoir can be completely emptied by axially shifting the piston being arranged in the intermediate reservoir in the direction of the outlet section.

Such a complete emptying furtherly avoids an undesired crystallization or the deposition of residues of the pharmaceutical product on the intermediate reservoir wallings and/or the piston wallings, whereby, on one hand, the exactness of dosing each single dose and, on the other hand, the function of the inventive device would be endangered.

A particular embodiment of the inventive device which makes it possible to emit single dose from the intermediate reservoir in an reproducible and untroubled way, is characterized in that the intermediate reservoir is formed in a cylindrical way and comprises a subsequent end section being conically shaped and directing to the outlet section, whereby the end section is connected with the outlet section by the afore described conduct. In this development, the form of the piston moreover corresponds to the form of the afore described intermediate reservoir, so that correspondingly the piston comprises a cylindrical piston section and an end section being conically formed and being connected with the cylindrical piston section. If in this embodiment of the inventive device additionally the connecting conduct being located between the vessel and the intermediate reservoir extends through the piston section up to the conical piston point, not only the complete emptying is guaranteed to a high degree in such a development of the inventive device, but also the reproducible filling of the intermediate reservoir.

In respect to the formation of the conical end section, there are several possibilities. This conical piston end section can, for example, consist of the same material as the rest of the piston, whereby, however, in a particularly advantageous embodiment the conical piston end section can be formed by a conically extending jacket tube being closed at its end which is located opposite to the piston section. The connecting conduct then extends almost over the whole axial length of the jacket tube, whereby the connecting conduct is located between the vessel and the intermediate reservoir, and whereby the conically shaped jacket tube comprises outlets for the liquid advanced from the vessel on its jacket surface. Hereby it is guaranteed that the intermediate reservoir is impeccably filled with the single dose of the liquid pharmaceutical product coming from out of the vessel.

The inventive device basically makes it possible to parenterally apply the single dose of the liquid pharmaceutical product being located in the intermediate reservoir directly over the outlet section connected with the intermediate reservoir by means of the conduct by submitting the single dose of the liquid pharmaceutical product to a high pressure. It is particularly suitable, however, when the outlet section comprises a mounting section for the detachable fixing of a cannula in such a way that the conduct can be connected with the cannula in a liquid-tight manner. In this embodiment of the inventive device, the mounting section thus holds a cannula which can be detachably fixed and which, during the application of the liquid pharmaceutical product, penetrates the body zone chosen by the user and then effectuates the parenteral application of the product.

A further embodiment of the inventive device is characterized in that additionally the afore described closing element which effectuates a closing of the conduct being located between the intermediate reservoir and the outlet section during the filling of the intermediate reservoir can be detachably fixed at the mounting section. Depending on the formation of the mounting section and the closing element, the closing element and the cannula can either be fixed at the same time at the mounting section or the closing element and the cannula can be fixed optionally at the mounting section, whereby the latter mentioned possibility is preferred since hereby the risk of getting hurt by removing the closing element is avoided by cannula still being fixed at the mounting section.

Another embodiment of the inventive device is characterized in that moreover the mounting section comprises a protecting element, whereby this protecting element then covers a cannula fixed at the mounting section at least partially or completely. This protecting element protecting the respective user from an undesired hurting by the cannula can hold the closing element or additionally support the fixing of the closing element at the mounting section, so that hereby a handle section is formed which the user touches while preparing the inventive device for the application.

A further particularly suitable embodiment of the inventive device comprises first cylinder being located in the casing and a second cylinder surrounding the first cylinder, whereby the first cylinder and the second cylinder are axially shiftable relative to the casing. The section for taking up the vessel, particularly the afore described carpule, is arranged within the first cylinder, whereas the intermediate reservoir being connected with the vessel is arranged within the second cylinder. In this embodiment of the inventive device, the first cylinder and the second cylinder can be axially shifted from a first position in which the cannula being fixable to the mounting section protrudes over the afore described protecting element, respectively the device casing, and in which the intermediate reservoir is emptied over the conduct and the cannula following hereafter, and a second position in which a cannula being fixable to the mounting section is covered by the protecting element and in which the intermediate reservoir is filled with the single dose, and vice-versa.

The afore described embodiment of the inventive device permits a parenteral application of the corresponding single dose of the liquid pharmaceutical product in a particularly simple way. Herefore it is only necessary to transmit the first cylinder and the second cylinder from a first position in which the intermediate reservoir is empty into a second position by axially shifting the cylinders relatively to the casing. This axial shifting leads to the fact that the intermediate reservoir is filled with the liquid being drained out of the vessel. After attaching a corresponding cannula at the mounting section, the penetration of the cannula into the body zone of the user and the emptying of the intermediate reservoir is carried out by axially shifting both cylinders in the direction of the mounting section, whereby as a consequence the single dose is parenterally applied. Both cylinders are preferably formed in that way that they additionally can be axially shifted relatively to each other, so that there is a time difference between the actual penetration procedure of the cannula into the body zone of the user and the emptying of the intermediate reservoir, whereby it is made possible to apply the liquid pharmaceutical product in a corresponding time retardation.

In order to cause the afore described axial shifting of both cylinders from the first position into the second position and from the second position into the first position, these axial shiftings can be realized manually in both directions. This means, however, that, when the respective user transmits both cylinders from the second position into the first position in the afore mentioned way, the penetration of the cannula into the body zone has to be carried out manually by the user himself, which the user considers to be extremely unpleasant and difficult. For that reason a particularly advantageous development of the afore described embodiment of the inventive device is characterized in that the first cylinder and the second cylinder comprise each a spring in such a way that in the second position of the cylinders both springs are tensioned and that in the first position of the cylinders the springs are released.

In order to fix both cylinders in their second position being tensioned by the corresponding springs, each cylinder in the inventive device can comprise a corresponding locking element. By releasing the locking of the second cylinder, the second cylinder is then transmitted from the second position into the first position caused by the spring power of the spring located at the second cylinder, which causes an inevitable penetration of a cannula being fixed at the mounting section into the chosen body zone of the user, whereby the user has no influence on this. Subsequently the locking being provided for the first cylinder is released, whereby the first cylinder is axially moved in the direction of the outlet section by the spring being provided for the first cylinder, whereby the intermediate reservoir is emptied, so that the corresponding single dose of the liquid pharmaceutical product is parenterally applied.

According to a particularly suitable and easy to handle development of the embodiment of the inventive device, both cylinders are fixable in the second position by a single locking element. This means that the user has to release only one locking element in order to commonly transmit both spring-tensioned pistons being fixed in the second position into the first position, whereby the penetration procedure of the cannula into the body zone and the injection of the single dose takes place.

In order to obtain in the afore described embodiment of the inventive device that firstly the penetration of the cannula into the body zone takes place and hereafter the injection of the single dose, a particularly suitable development of this embodiment is characterized in that it comprises springs corresponding to each other in respect to their characteristic spring line. Hereby the spring provided for the second cylinder has a steeper characteristic spring line than the spring being located at the first cylinder, so that the already afore mentioned time retardation between the penetration of the cannula and the subsequent injection can be regulated by accommodating the characteristic spring lines to each other in a high range.

A further advantageous embodiment of the inventive device is directed to a first cylinder and a second cylinder surrounding the first cylinder being arranged within the casing, whereby the first cylinder and the second cylinder are axially shiftable relatively to the casing. The section for taking up the vessel, preferably the afore mentioned glass carpule, is arranged within the first cylinder, whereas the intermediate reservoir connected with the vessel is arranged within the second cylinder in such a way that the first and the second cylinder can be commonly and axially shifted from a first position in which the cannula being fixable to the mounting section protrudes over the protecting element, respectively the casing, and in which the intermediate reservoir is emptied, into a second position in which a cannula being fixable to the mounting section is covered by the protecting element, and vice-versa. For filling the intermediate reservoir the first cylinder can be axially shifted into a third position in the direction of the vessel relatively to the second position of the second cylinder.

In other words, this afore described and particularly advantageous development of the inventive device is characterized in that it provides also a third position, contrarily to the afore described embodiments of the inventive device in which the cylinders can only be arranged in a first and a second position.

In order to use the inventive device, firstly both cylinders are transmitted from the first position into the second position, which causes that a cannula being fixed at the mounting section is covered by a protecting element. At this time the intermediate reservoir is not yet filled with the single dose of the liquid pharmaceutical product. Subsequently the first cylinder is axially shifted into a third position relatively to the second cylinder which remains in the second position, whereby the intermediate reservoir is completely filled with the liquid pharmaceutical product being drained out of the vessel by the connecting conduct. As the first cylinder is moved from the second position into the third position, the conduct connecting the cannula with the intermediate reservoir is blocked in an airtight way by one of the afore described valves or by the also afore mentioned closing element. A vacuum causing the liquid flow from the vessel into the intermediate reservoir is thus generated in the intermediate reservoir.

Hereafter the ready-to-operate device is brought into contact with the chosen body zone, so that then the user moves the second cylinder from the second position into the first position, whereby the penetration procedure of the cannula into the body zone is manually effectuated. Hereafter the user moves the first cylinder from the third position into the first position, whereby the corresponding injection of the single dose of the liquid pharmaceutical product from the intermediate reservoir into the body is caused.

As it is, however, mentioned above, some users have the problem with this application that they have to carry out themselves the corresponding injection of the single dose of the liquid pharmaceutical product from the intermediate reservoir into the body. In order to avoid this, a further development of the afore described embodiment of the inventive device is characterized in that each cylinder (first cylinder, second cylinder) comprises a spring, whereby a first spring pre-tensions the arrangement of the cylinder in the third position and a second spring pre-tensions the arrangement of the second cylinder in the second position. Moreover, the first cylinder is fixable in the third position by first locking and the second cylinder is fixable in the second position by a second locking in such a way that this fixing is caused by corresponding lockings can preferably be released by a single release button.

In order to apply such a device, the respective user transmits the second cylinder into the second position against the power of the corresponding second spring, whereby such an axial shifting of the second cylinder is realized preferably by a shifting element arranged at the outside of the casing. Concurrently to operating this shifting element, the first cylinder is shifted into its second position against the power of the first spring, whereby then the second locking fixes the second cylinder in the second position. When the shifting element is furtherly operated, the first cylinder is axially shifted relatively to the second cylinder from the second position into the third position against the power of the corresponding first spring and is then fixed in the third position by the first locking.

By operating the common release button both cylinders are axially shifted from the third position (first cylinder), respectively from the second position (second cylinder), into the first position as a result of the spring power of the first and the second spring, whereby the penetration of the cannula into the body zone and the injection of the single dose from the intermediate reservoir is forcibly effectuated without being influenced by the user.

A further development of the afore described embodiment is preferably characterized in that, by operating the release button, firstly the second locking fixing the second cylinder in the second position is released and then the first locking fixing the first cylinder in the third position is released in a corresponding time retardation.

The afore described inventive device are particularly used in the initially discussed inventive sale unit, whereby, however, the inventive device can be traded on the market independently from the sale unit.

Furthermore, the present invention is directed to a refill unit to be employed in the initially described inventive sale unit or in the afore discussed inventive device.

Hereby this inventive refill unit comprises at least one cannula as well as at least on vessel filled with the liquid pharmaceutical product, whereby the vessel can be arranged within the afore described inventive device and emptied in single doses by means of this device.

The inventive refill unit has the essential advantage of being perfectly adjusted to the afore described sale unit as well as to the inventive device in respect to its constructive features, so that the user of the afore described inventive sale unit or of the afore discussed inventive device can apply the inventive refill unit when a longer parenteral application of the liquid pharmaceutical product is required from the medical point of view and when the vessel being filled with the liquid pharmaceutical product and being provided in the afore described inventive sale unit is emptied.

A first development of the inventive refill unit is characterized in that a detaching element to remove the emptied vessel from the inventive device for emitting a given liquid amount in single doses is arranged in the refill unit. The detaching element is formed correspondingly to the respective form of the section for taking up the vessel filled with the liquid pharmaceutical product, this section being located within the casing of the inventive device, whereby this detaching element preferably comprises a grip section so that the user can grip the detaching element and a fixing section for the form-fit and/or non-positive fixing of the emptied vessel.

As already described above in the inventive sale unit, a first embodiment of the inventive refill unit is characterized in that the unit comprises a number of cannulas that correspond to a number of the single doses of the pharmaceutical product. Hereby the user can exchange the used cannula for a corresponding sterile cannula after each parenteral application of the liquid pharmaceutical product, whereby the risk of an infection is avoided. The cannulas provided in the refill unit are preferably constructed in that way that the actual needle of the cannula is protected by a solid plastic jacket, whereby this solid plastic jacket, on one hand, guarantees the sterility of the needle and, on the other hand, keeps the user from unintentionally hurting himself with the needle. Such an embodiment of the refill unit particularly comprises ten of the afore described cannulas, whereby then the vessel being provided in the refill unit and being filled with the liquid pharmaceutical product makes it possible to correspondingly apply ten single doses of the product to be parenterally applied.

In order to make it again easier for the user to operate the inventive refill unit during the parenteral application, a further advantageous development is directed to a refill unit that comprises a number of cannulas that correspond to a number of sponges, whereby these sponges are moistened with a disinfectant, as for example a low alcohol (ethanol, propanol). In order to avoid on the sponges an undesired evaporation of the disinfectant, the sponges moistened with a disinfectant are wrapped singly in corresponding foils, preferably plastic foils and more particular compound plastic foils, so that, for the parenteral application, the user removes just one sponge from the wrapping and disinfects herewith the spot chosen for the injection.

In another embodiment of the inventive refill unit, the unit additionally comprises a section serving to take up the used cannulas and/or used sponges. Hereby this section to take up the used cannulas, respectively the used sponges, is formed in the way that the used cannulas, respectively sponges, cannot fall out of the refill unit while being used, so that the section is formed particularly as a separately closable section. If in the refill unit this section is formed as a section being detachable from the refill unit, as for example as a closable box, the used cannulas and, if necessary, the sponges can be separately wasted, as for example by the special trade, as far as this is required by legal prescriptions.

The inventive refill unit can comprise basically each vessel containing the multitude of single doses of the liquid pharmaceutical product, as far as it is guaranteed that this vessel is formed in that way that it can be set into the device and emptied in single doses by means of the device. However, it is particularly suitable to fill the liquid pharmaceutical product to be parenterally applied by the user in single doses in a cylindrical or cylinder-like glass carpule, whereby such a glass carpule holds particularly between about 1.5 ml and about 8 ml, preferably between about 2 ml and about 6 ml, of the liquid pharmaceutical product.

A particularly advantageous development of the afore described glass carpule is characterized in that in the inventive refill unit such a glass carpule is arranged which is closed, at its bottom side, by a piercable membrane and, at its top side, by a plug being formed in that way that it can be axially shifted within the glass carpule in the direction of the piercable membrane when the liquid level is descending. This special development of the glass carpule has the particular advantage that the bottom section of the plug is located in the immediate proximity of the liquid level or even contacts the liquid level, so that there is no air puffer above the respective liquid level when the liquid level is descending because of the single doses emitted. On one hand, this avoids an undesired oxidative modification of the respective liquid pharmaceutical product and, on the other hand, the special forming of the plug effectively avoids the formation of a vacuum in the glass carpule when the liquid amount is decreasing, whereby such a vacuum would have a negative effect on the exactness of the liquid amount emitted in single doses.

In order to ensure the required tightness between the plug and the inner walling of the glass carpule, according to the afore described embodiment of the glass carpule which disposes of the afore described plug being axially shiftable in the direction of the piercable membrane, a further development of the inventive refill unit is characterized in that the plug comprises on its jacket surface at least one, preferably two to five, disk-like sections directing radially to the outside. Hereby these disk-like sections can be deformed when the plug is inserted into the glass carpule with the form ation of a sealing surface which liquid-tightens and air-tightens the inner surf ace of the carpule. The disk-like sections directing to the outside are preferably dimensioned in that way that an end section of the disk-like sections is elastically deformed by the axial shifting of the plug in the glass carpule opposite to the shifting direction with the formation of a correspondingly larger dimensioned sealing surface. In respect to the material that the plug consists of, it is to be noted that herefore preferably an elastic, chemically resistant plastic material or rubber material is chosen, whereby herefore a halogenbutyl-rubber proved to be particularly suitable.

When the afore described plug can be axially shifted within the glass carpule by a power of less than 10 N, preferably by a power of between 4 N and 8 N, it is particularly guaranteed that the above described advantages occur in a particularly reproducible way.

By using the inventive refill unit in connection with the inventive device of the inventive sale unit, basically all liquid pharmaceutical products being stable in storage can be parenterally applied by the user himself. Hereby the term liquid pharmaceutical products means all such products which, as actual product, are liquid or from which stable solutions, stable dispersions or stable emulsions can be manufactured in an organic or inorganic, physiologically safe liquid. The afore described vessel or the afore described and particularly used glass carpule preferably comprise an aqueous solution of a heparin, preferably an aqueous solution of a low-molecular heparin, and particularly an aqueous solution of an enoxaparin-sodium. Such a refill unit is then used by such users who, because of their syndrome and from the medical point of view, have to apply the heparin daily in constant single doses for a longer time period, in order to prevent, for example, the risk of a thrombosis after having discharged the user from the hospital. A further preferred employment of the inventive refill unit is the regular parenteral application of a given and constant amount of a growth hormone, whereby, for this case of application, the vessel and particularly the afore described glass carpule is filled with a solution of the growth hormone, preferably an aqueous solution of the growth hormone.

The inventive sale unit, the inventive device as well as the inventive refill unit will be described in detail by embodiments in connection with drawings as follows, in which like reference numerals designate the same elements.

DETAILED DESCRIPTION OF THE INVENTION

Figure 1:
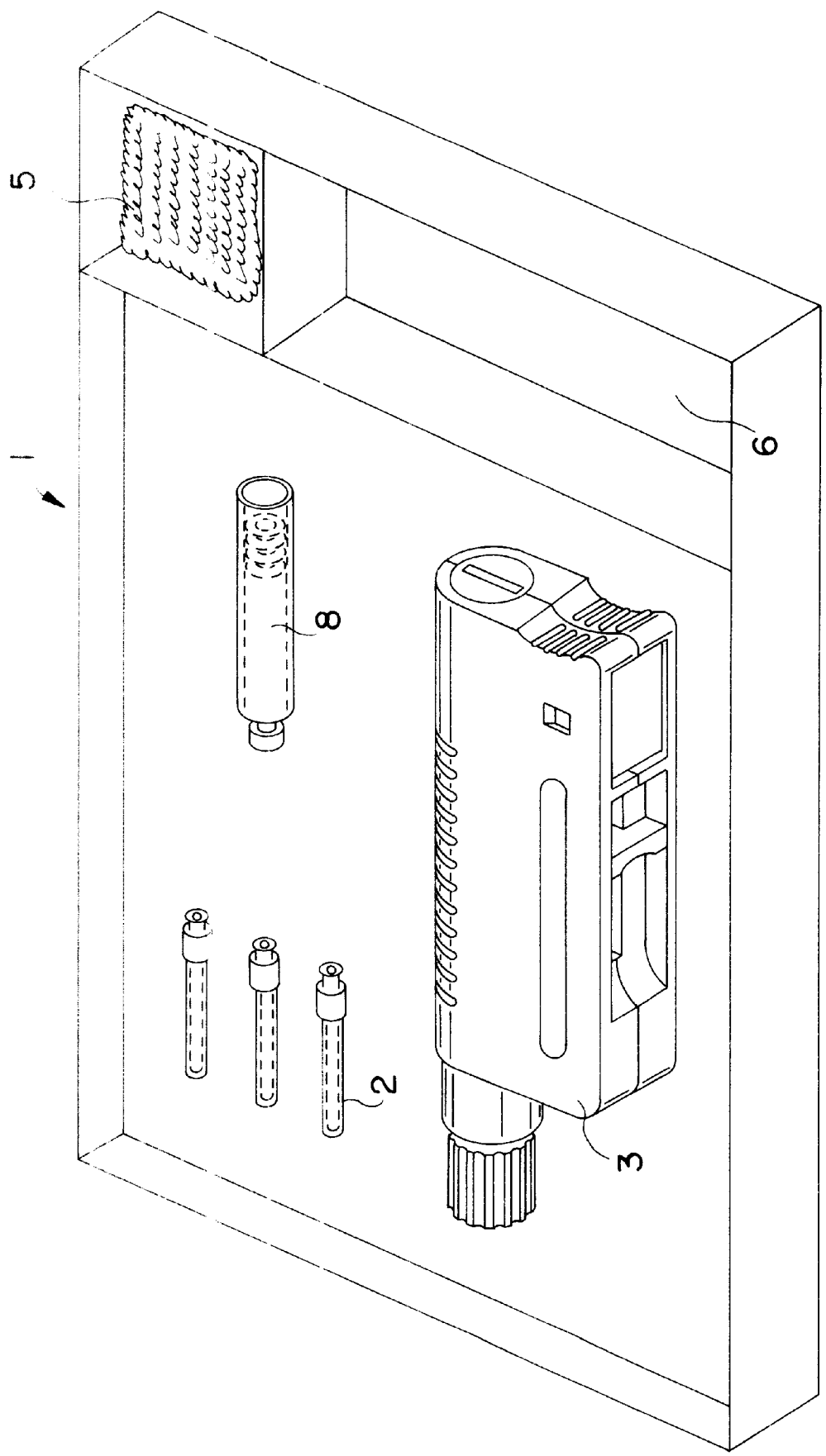
FIG. 1 is a perspective view of an embodiment of the sell unit.

A sale unit collectively designated with 1 and shown in FIG. 1 comprises a device 3 for emitting a given liquid amount of the pharmaceutical product, a multitude of cannulas 2 being provided with a corresponding cannula protector 45 (FIG. 3) for the sterile storing, a glass carpule 8 serving as vessel being filled with the liquid pharmaceutical product. Moreover, the sale unit 1 comprises a number of sponges 5 moistened with an disinfectant, whereby the number of sponges 5 corresponds to the number of the cannulas 2. The sale unit 1 furthermore contains a section 6 taking up used cannulas, whereby, according to the embodiment shown in FIG. 1, this section can be closed by a cover which is not shown. This section 6 is collectively arranged at the sale unit 1 in a detachable way, so that, after taking up the used cannulas, this section 6 can be separately wasted, as far as this is legally prescribed or desired. The sale unit 1 usually comprises 10 cannulas 2, so that correspondingly the glass carpule 8 contains the liquid amount for 10 cannulas. Usually the liquid amount emitted each in single doses varies between 0.1 ml and 1 ml, so that correspondingly the glass carpule contains between 1 ml and 10 ml of the liquid pharmaceutical product. In order to avoid an evaporation of the disinfectant of the sponges 5, each sponge 5 is separately wrapped by a corresponding plastic foil in an air-tight way. The sale unit 1 taking up the afore described parts is collectively closed by a cover (not shown) or is arranged in the usual plastic wrapping, if necessary even in a sterile way.

Figure 2:
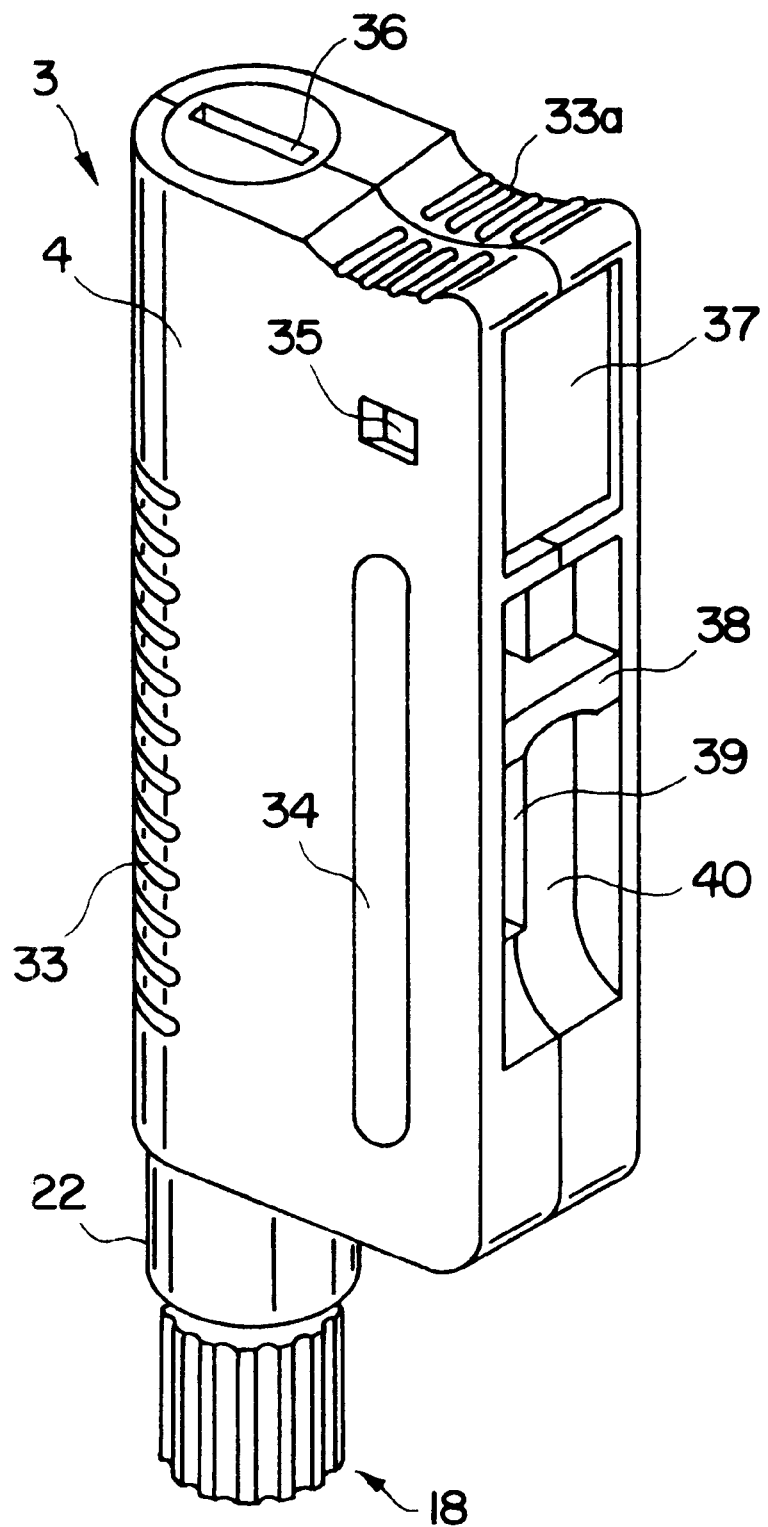
FIG. 2 is a perspective, schematical view of the device for emitting a given liquid amount in single doses.
Figure 3:
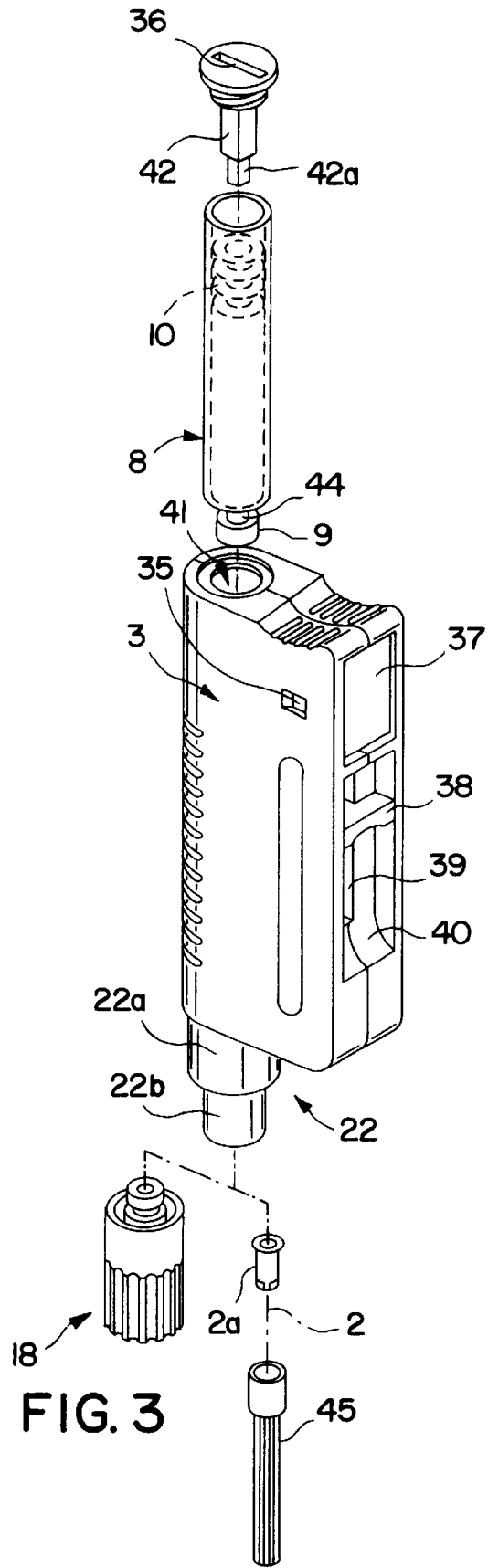
FIG. 3 is an explosion drawing of FIG. 2.

The device 3 for emitting a given liquid amount of the liquid pharmaceutical product, the device 3 being shown in detail in FIG. 2, comprises a protecting element 22, whereby this protecting element 22 consists of a outer cylinder 22a and inner cylinder 22b being concentrically arranged relative to the outer cylinder 22a which are manufactured from a transparent plastic material and which can cover a cannula 2 fixed at the device 3, as this is shown, for example, in FIG. 3. Furthermore, the device 3 comprises a casing 4, whereby an upper grip section 33, a window 34, a counting device 35, a second grip section 33a, a cover 36 being detachable from the casing, a release button 37, a shifting element 38 being fixed by a corresponding slot 39, as well as a deepening 40 are arranged at the casing 4.

Figure 4:
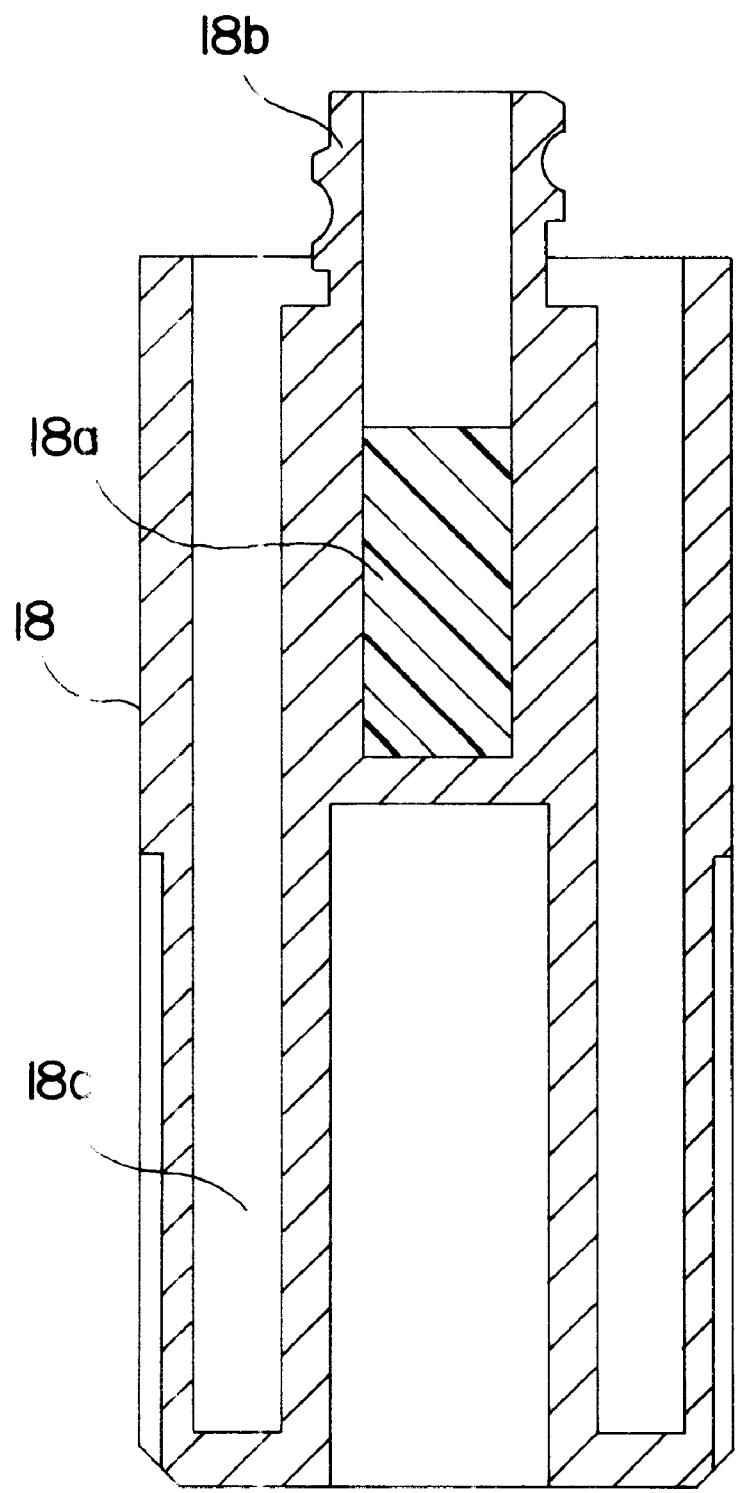
FIG. 4 is an enlarged schematical sectional view of a closing element.

In the device 3 shown in FIG. 2 furthermore a closing element 18 is fixed at the casing 4, whereby the closing element 18 is subsequently described in detail in connection with FIG. 4. The user can thus easily hold the device 3 at the grip sections 33 and 33a as well as at the closing element 18. The afore mentioned counting device 35 serves to count the single doses of the liquid pharmaceutical product emitted by means of the device 3, whereas the window 34 arranged in the casing makes it possible to control the liquid level in the glass carpule 8, as far as the glass carpule 8 is taken up by the device 3, whereby the cover 36 is removed in order to arrange the glass carpule 8, as this is shown in FIG. 3.

FIG. 3 schematically shows the insertion of the glass carpule 8 into the device 3 and the arrangement of the closing element 18 as well as the arrangement of a cannula 2. During the insertion of the glass carpule the cover 36 is firstly removed in order to open the section 41 taking up the vessel filled with the liquid pharmaceutical product, whereby this section 41 is located within the casing 4. When the glass carpule 8 has been inserted into the section 41, the corresponding opening is closed with the cover 36. At its bottom side the cover 36 comprises an axially extending lengthening pin 42 ending in an end section 42a, whereby the lengthening pin 42 and the end section 42a can be axially shifted together with the cover 36.

In a further, not shown and preferably used embodiment the lengthening pin 42 and the section 42a are axially shiftable in the direction of the arrow 51 relative to the cover 36 so that after fixing the cover 36 on the casing 4 an axial shifting of the lengthening pin 42 and the section 42a can be reached by a manual operation done by the user independent of the kind in which the cover 36 is fixed on the casing 4.

This axially shifting is done by the user by forcing a section of the lengthening pin 42 protruding over the cover 36 when the cover is fixed.

Figure 7:
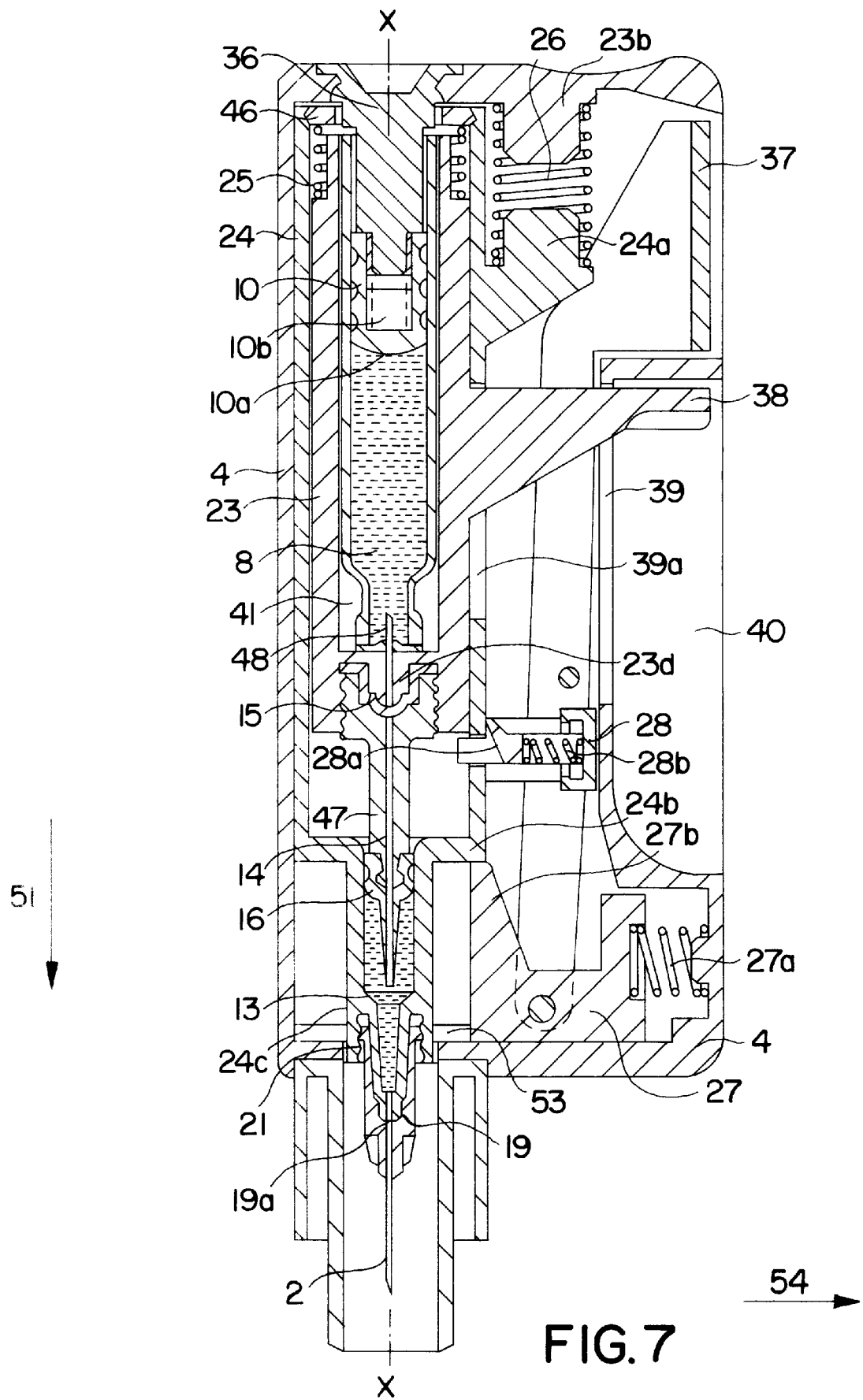
FIG. 7 is as FIG. 6, but with filled intermediate reservoir.

This end section 42a can gear into a deepening being correspondingly carved into a plug 10, whereby the glass carpule 8 can be submitted to a power being axially directed downward can be, as soon as the glass carpule 8 is arranged in the section 41 and the cover 36 is screwed onto the corresponding opening or fixed by means of a bayonet closing. At its bottom side the glass carpule 8 filled with the liquid pharmaceutical product is closed by a piercable membrane 9 being fixed by a bead in connection with a metal strap 44 in the usual way. A cannula 2 or the closing element 18 can be optionally fixed at a mounting section 21 (for example as shown in FIG. 7) by a corresponding weight, as these options are shown in FIG. 3. Hereby the cannula 2 is surrounded by a cannula protector 45 which makes it possible for the user not to hurt himself when he operates the cannula 2. The cannula protector 45 can be clamped onto the base section 2a of the cannula 2 and, if necessary, fixed at the base section 2a by a thread.

The cylindrical closing element 18 (FIG. 4) comprises a sealing element 18a which can contact a conduct outlet 19a (FIGS. 5 and 6) and which can close the conduct outlet in an air-tight and liquid-tight way, as soon as the closing element 18 is fixed at the mounting section 21 by a corresponding thread 18b. Moreover, the closing element 18 comprises a slot section 18c to take up the walling of the inner cylinder 22b of the protecting element 22.

Figure 5:
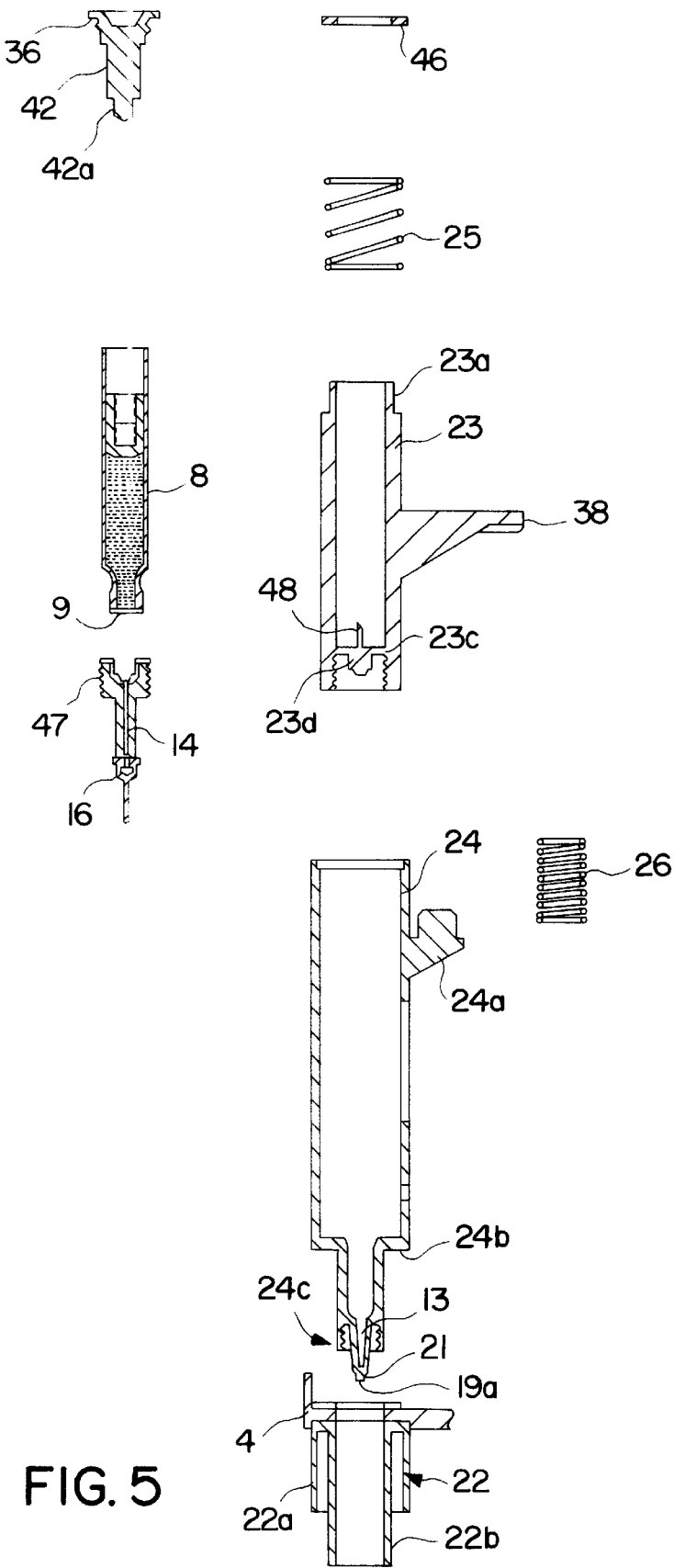
FIG. 5 is an sectional explosion view of the axially shiftable cylinder.

The schematical explosion view of FIG. 5 shows the essential interior parts of the device 3. These are a first, inner cylinder 23, a second, outer cylinder 24, whereby the second cylinder end 24b with its bottom side in the mounting section 21 to which a cannula 2 or the closing element 18 can be optionally fixed. In this section the protecting element 22 is detachably mounted at the casing 4 which is only partially shown in FIG. 5. The first cylinder 23 is provided with a first spring 25 and the second cylinder 24 is provided with a second spring 26, whereby the first spring 25 extends between an upper section 23a of the first cylinder 23 and a ring element 46 being fixed at the second cylinder 24, whereas the second spring 26 is supported by an lower bearing 24a being located at the second cylinder 24 and an upper bearing 23b being located at the casing 4. The shifting element 38 is formed as on piece with the first cylinder 23.

Furthermore, the first cylinder 23 comprises a bottom plate 23c being provided with a projection 23d at its bottom side. The shaft 47 of a piston 16 can be connected with this projection 23d, so that the piston 16 is fixed at the first cylinder 23 and moved together with the first cylinder 23. A connecting conduct 14 extends within the shaft 47 and within the piston 16, whereby this connecting conduct 14 is guided also by the bottom plate 23c and the projection 23d and ends in a hollow needle 48.

If then the glass carpule 8 filled with the liquid pharmaceutical product is set into the inner space of the first cylinder 23, the inner space forming the section 41 taking up the vessel, and if hereby the glass carpule 8 is submitted to a pressure in the direction of the mounting section 21 by means of the plug and the lengthening pin 42, respectively the end section 42a, the hollow needle 48 pierces the piercable membrane 9 of the glass carpule 8, so that the connecting conduct 14 is connected to the content of the glass carpule 8. Hereby the connecting conduct 14 is provided with a reflux valve 15 in the section connecting the shaft 47 with the projection 23d, whereby this reflux valve 15 is shown enlarged in FIG. 8.

Figure 8:
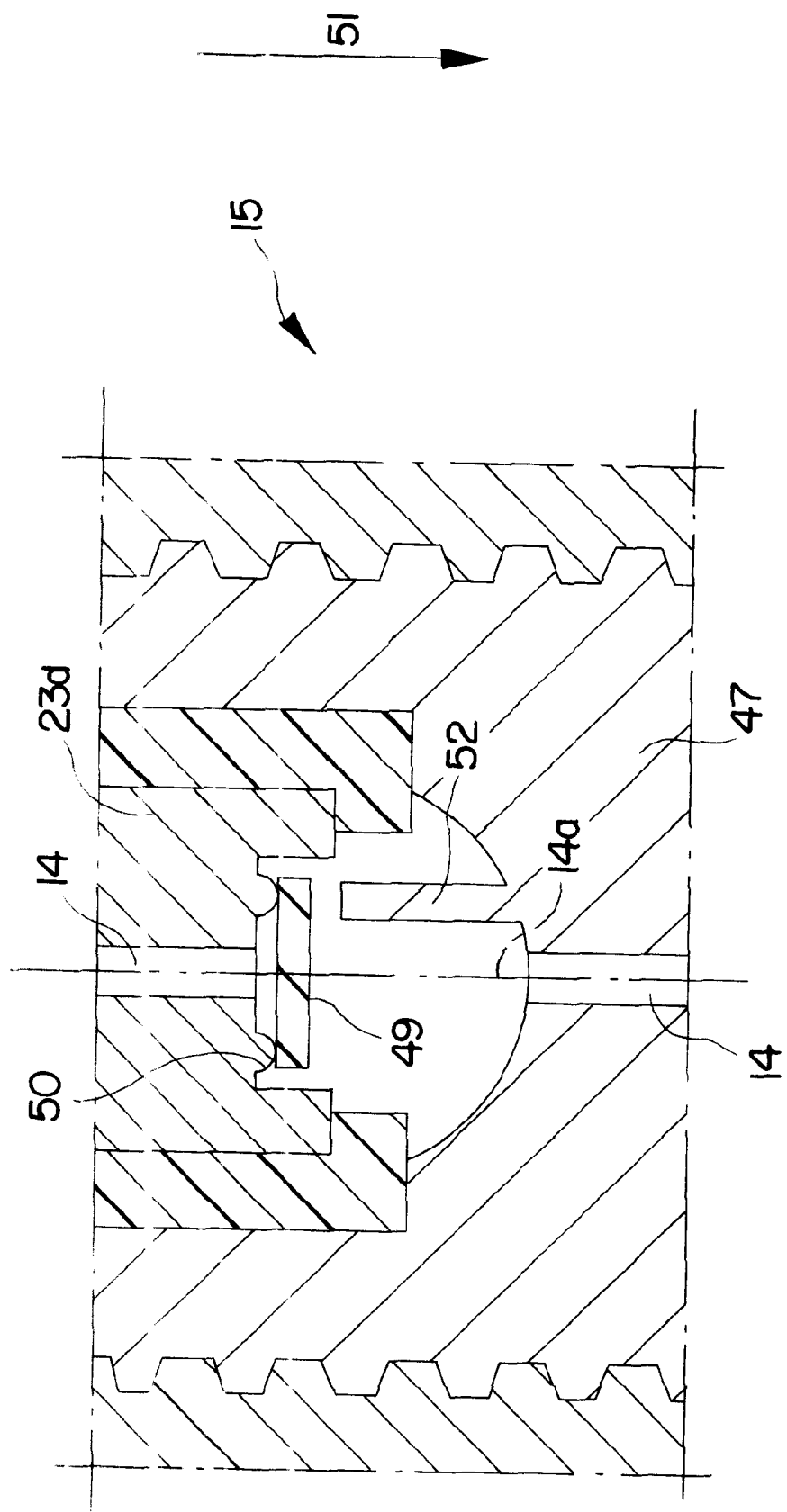
FIG. 8 is an enlarged schematical sectional view of a reflux valve.

This reflux valve 15 comprises, according to FIG. 8, a disk-like, round sealing membrane 49 being held by a ring bearing 50. A section which is superfused by the liquid and which enlarges the conduct inlet 14a of the connecting conduct 14 is arranged underneath the sealing membrane 49. If the liquid flows in the direction of the arrow 51, as this is required in the conduct 14 for the filling of the intermediate reservoir, the sealing membrane 49 is lifted from the ring bearing 50 and does thus not block the flow of the liquid. Hereby this movement of the sealing membrane 49 is limited by four radially arranged linking elements 52, so that it is avoided that the sealing membrane 49 closes the enlarged conduct inlet 14a. If the liquid flows in the opposite direction of the arrow 51, the sealing membrane 49 is brought into a position in which it seals the ring bearing 50, so that hereby a flow in the opposite direction of the arrow 51 is avoided without risking an adhesion of the sealing membrane 49.

Figure 6:
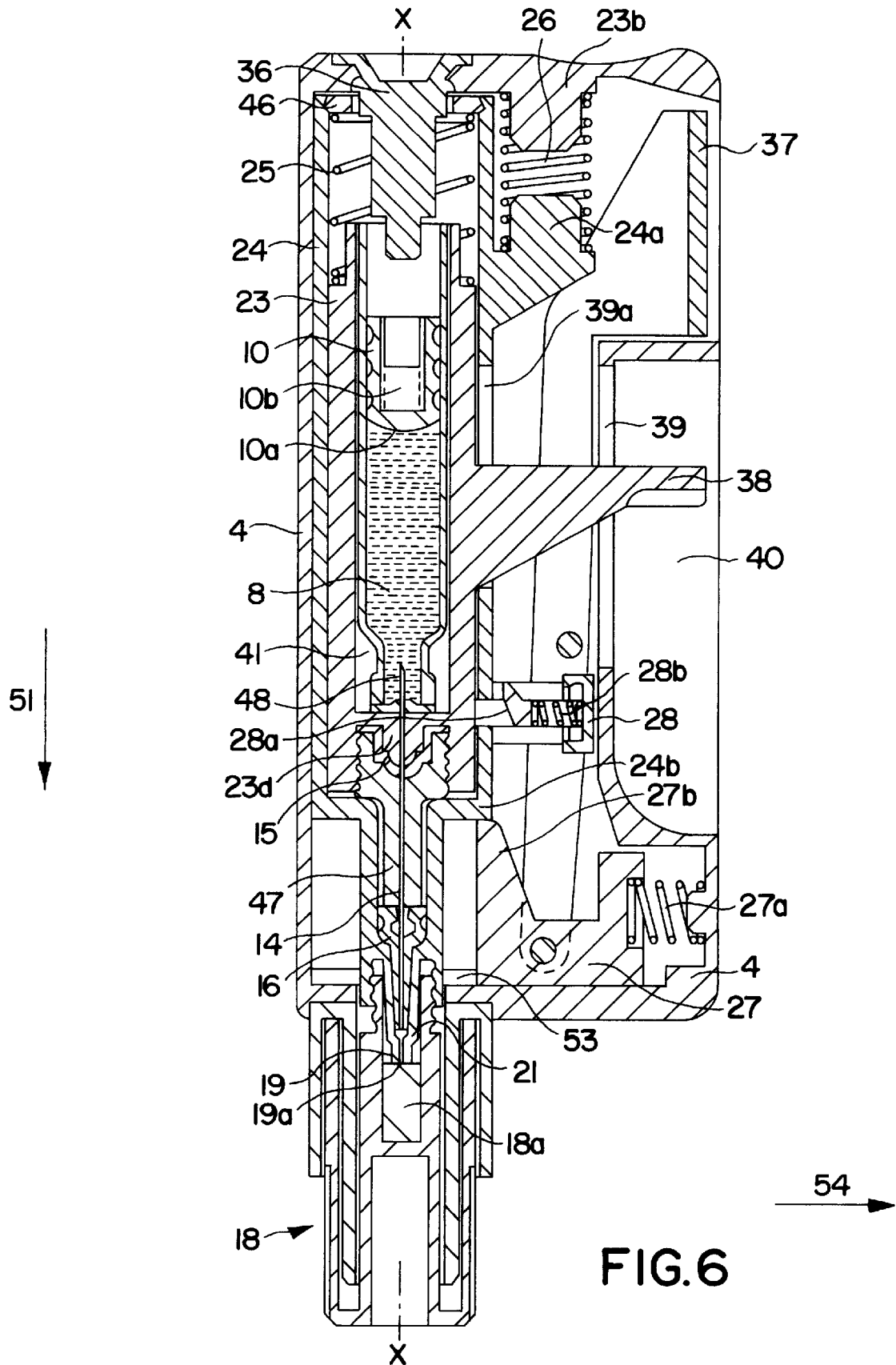
FIG. 6 is a sectional view of a first embodiment with emptied intermediate reservoir.

In FIGS. 6 and 7 the same embodiments are shown, however, in different operating situations. Hereby FIG. 6 shows the device in a situation in which the intermediate reservoir 13 is empty, whereby in this situation the single dose of the liquid pharmaceutical product has thus been parenterally applied, and in which the respective user finds the device in order to then prepare it for the next single dose. In FIG. 7 the intermediate reservoir 13 is filled with a single dose of the liquid pharmaceutical product being supplied from the glass carpule 8 over the conduct 14. In the operating situation shown in FIG. 7 a cannula 2 is furthermore fixed at the mounting section 19, so that FIG. 7 as a whole shows the device in an operating situation occurring immediately before the parenteral application of the single dose of the liquid pharmaceutical product by the user.

The parts shown in FIG. 5 and described above are provided as well in the FIGS. 6 and 7 and designated with the same reference numbers.

In the first cylinder 23 the glass carpule 8 is arranged in the adequate section 41, whereas the second cylinder 24 forms the intermediate reservoir 13 in its bottom section 24c (also FIG. 5).

Starting from the operating situation shown in FIG. 6 in which the closing element 18 is fixed at the mounting section 21 and in which the closing element 18a closes the conduct outlet 19a of the conduct 19 which connects the intermediate reservoir with the conduct outlet, the first cylinder 23 and the second cylinder 24 were commonly transmitted from a first position not shown, in which the spring 25 is released and in which the second cylinder 24 contacts a casing section 53 by means of the recessing section 24b (FIG. 5), into a second position as this is shown in FIG. 6, whereby this transmitting was realized by axially shifting both cylinders in the opposite direction of the arrow 51 and relatively to the casing 4. In this second position the spring 25 being released in the first position of both cylinders is thus tensioned, whereby a fixing of this second position is realized by a second locking 27 gearing in at the recessing section 24b.

This common axial shifting of both cylinders 23 and 24 is caused by manually operating the shifting element 38 arranged at the outside of the casing, whereby this axial shifting of the shifting element 38 is guided through a slot 39 (FIG. 3) located in the casing 4.

In order to fill the intermediate reservoir 13 in this second position with a single dose of the liquid pharmaceutical product supplied by the glass carpule 8 arranged within the first cylinder 23, the first cylinder 23 is shifted into the third position in the opposite direction of the arrow 51 and relatively to the casing 4 and to the second cylinder 24 remaining in the second position, whereby this shifting is realized by means of the shifting element 38 against the power of the second spring 26, and whereby this third position is axially shifted in the opposite direction of the arrow 51, which is shown in FIG. 7.

In this third position of the first cylinder, the first cylinder 23 is fixed by a first locking 28 (FIG. 7).

Conditioned by the fact that the closing element 18 avoids a ventilation of the intermediate reservoir 13 by means of the conduct 19 as a result of the fluid-tight contacting of the sealing element 18a with the conduct outlet 19a, a vacuum is generated in the intermediate reservoir 13 when the first cylinder 23 is axially shifted from the second position into the third position. This depends on the fact that concurrently with the shifting of the first cylinder 23 the piston 16 which is fixed to the first cylinder 23 by piston shaft 47 is axially shifted in the opposite direction of the arrow 51. This vacuum generated in the intermediate reservoir 13 then causes a complete filling of the intermediate reservoir with exactly one single dose of the liquid pharmaceutical product being supplied from the glass carpule 8 by means of the connecting conduct 14 and the opened reflux valve 15 which is arranged in the projection 23d of the first cylinder 23 and which is shown in FIG. 8.

This axial shifting of the first cylinder from the second position into the third position relatively to the casing and to the second cylinder is made possible by providing the walling of the second cylinder with a slot-like guidance 39a through which a section of the shifting element 38 extends, whereby the shifting element 38 is formed in one piece with the first cylinder 23.

The closing element 18 is then replaced by a cannula 2, whereby the cannula 2 is gripped by user at the cannula protector 45 and the cannula 2 is screwed onto the mounting section 21. Hereafter the user removes the cannula protector 45, whereby the device is prepared to apply the single dose of the liquid pharmaceutical product.

With this object the respective user chooses a body zone and brings the bottom zone of the inner cylinder 22b of the protecting element 22 in contact with this body zone. By operating the release button 37 the second locking 27 is shifted in the direction of the arrow 54 against the spring power 27a, so that the first cylinder 23 and the second cylinder 24 are commonly and axially shifted relatively to the casing 4 in the direction of the arrow 51 by means of the spring 26. This leads to the fact that the point of the cannula 2 penetrates the chosen body zone of the user. During the common axial shifting of both cylinders 23 and 24, a projection 27b being located at the second locking 27 becomes in contact with a projection 28a being located at the first locking 28, whereby this causes a shifting of the first locking 28 also in the direction of the arrow 54 against the spring power of the spring 28b located at the first locking 28. Hereby the first cylinder 23 is released from its third position, so that it is also axially shifted in the direction of the arrow 51 by means of the spring 25. This again leads to the fact that the piston 16 being axially connected with the first cylinder 23 by the shaft 47 is axially shifted in the direction of the arrow 51 and that thus the single dose of the liquid pharmaceutical product located in the intermediate reservoir 13 is injected into the body zone by the cannula 2. The axial shifting of the first cylinder 23 is terminated by the recessing section 24b of the second cylinder 24 and by the axial movement of the second cylinder 24 through the casing section 53.

After the parenteral application the user pulls the cannula 2 out of the body zone by means of the device, attaches the cannula protector 45 on the cannula 2, unscrews the cannula 2 from the mounting section 21 and screw the closing element 18 onto the mounting section 21. Independently of the power performed hereby by the user, the first cylinder and the second cylinder remain either in the first position or both cylinders are transmitted into a position as it is shown in FIG. 6.

Figure 9:
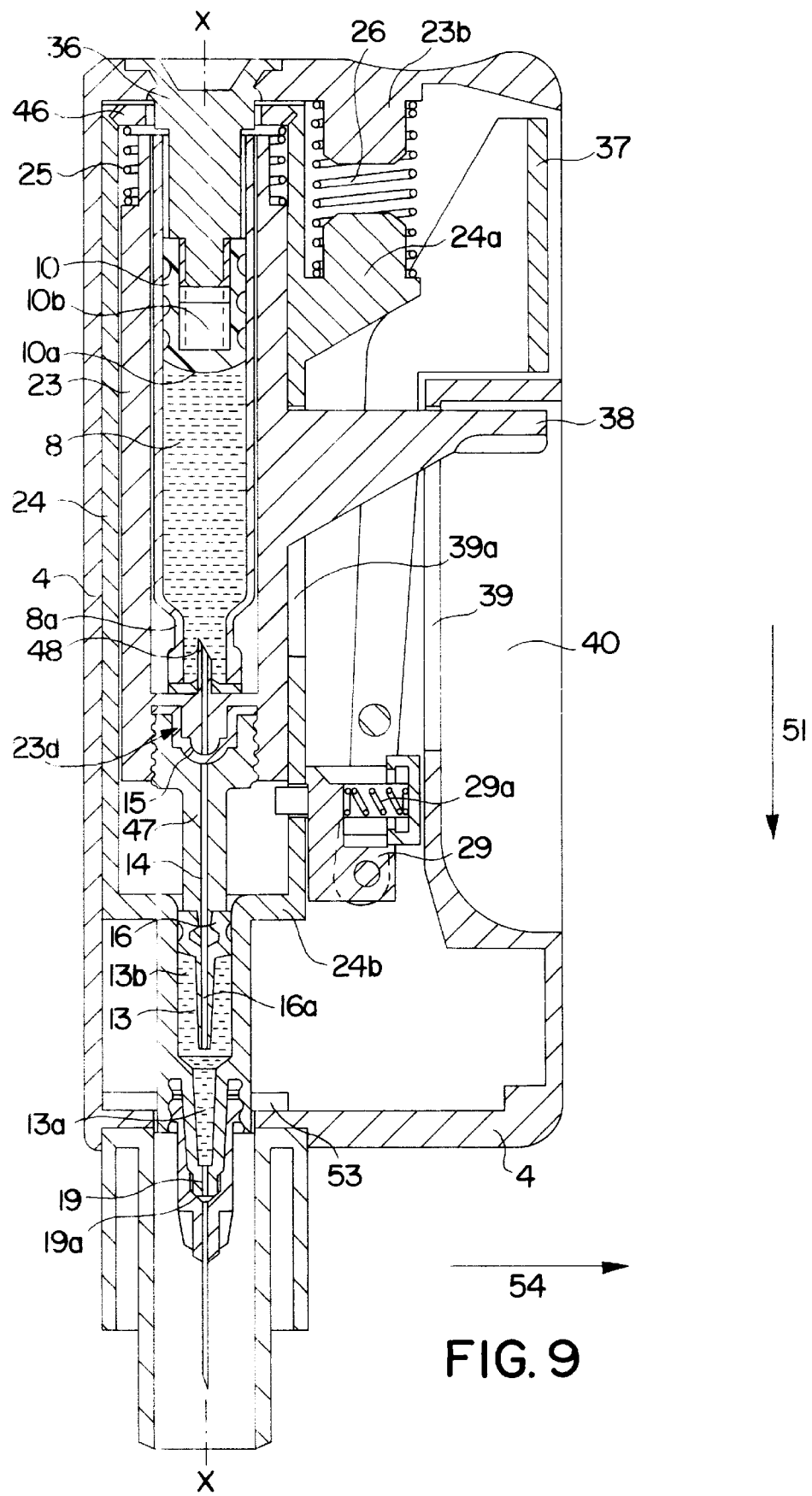
FIG. 9 is a sectional view of a second embodiment of the device with filled intermediate reservoir.

The second embodiment of the device, the embodiment being shown in FIG. 9, presents the device in such an operating situation in which the intermediate reservoir 13 is filled with the single dose of the liquid pharmaceutical product. The embodiment shown in FIG. 9 is thus ready to operate meaning that is ready to inject. Contrary to the embodiment described above in FIGS. 6 and 7, the embodiment shown in FIG. 9 is characterized in that both cylinders 23 and 24 can be axially shifted in the direction of the arrow 51 and vice-versa only between a first position (not shown) in which the first cylinder 23 contacts the recessing section 24b and the recessing section 24b contacts the casing section 53 and in which the intermediate reservoir 13 is emptied, and a second position as this is shown in FIG. 9 and in which the intermediate reservoir 13 is filled with the single dose. Moreover, the embodiment shown in FIG. 9 provides only a single locking 29 which fixes the first cylinder 23 and the second cylinder 24 in the second position and which can be released by means of the release button 37.

In order to make it possible in the embodiment shown in FIG. 9 to cause the time retardation between the penetration procedure of the cannula into the body zone of the user and hereafter the emptying of the intermediate reservoir 13 and thus the actual parenteral application of the single dose of the liquid pharmaceutical product, the characteristic spring lines of the springs 25 and 26 are adjusted to each other in such a way that the characteristic spring line of the spring 26 is steeper than the characteristic spring line of the spring 25. By operating the release button 37 the locking 29 is shifted in the direction of the arrow 54 against the spring power of the spring 29a, so that the locking 29 is released and that thus the first cylinder 23 and the second cylinder 24 can be commonly and axially shifted in the direction of the arrow 51 relatively to the casing. Caused by the steeper characteristic spring line of the spring 26, the second cylinder 24 projects, during the axial shifting, relatively to the first cylinder 23 the spring 25 of which has a more levelled characteristic spring line, over the first cylinder 23, so that the cannula 2 firstly penetrates the body zone and that then the first cylinder 23 and thus also the piston 16 connected with the first cylinder 23 by the shaft 47 transmits the single dose of the liquid pharmaceutical product from the intermediate reservoir 13 into the body zone of the user.

In order to guarantee in the afore described embodiment of the inventive device a complete emptying of the intermediate reservoir, the intermediate reservoir 13 comprises a cylindrical section 13b and a subsequent conical section 13a (FIG. 9), whereby the outlet of the conical section 13a opens into the conduct 19, as this can be seen perfectly in FIG. 9. The piston 16 being axially shiftable within the intermediate reservoir 13 correspondingly comprises a cylindrical piston section and conical piston section 16a directed to the conduct 19, whereby this conical piston section is formed by a corresponding conically-shaped jacket tube surrounding the outlet of the connecting conduct 14. This jacket tube is closed at its bottom side and it comprises outlets on its conical surface, so that by these outlets the liquid supplied by the conduct 14 is transported into the intermediate reservoir. When the piston is axially lowered in the direction of the arrow 51, the conical piston section 16a displaces the liquid located in the intermediate reservoir 13 in that way that the conical piston section 16a enters the conical cylinder section 13a and thus fills it completely.

It is even possible to provide an intermediate reservoir 13 which does not comprise the afore described and especially in FIG. 9 shown conical section 13a or which comprises a conical section 13a having restricted length. In other words in this embodiment the cylindrical section 13b of the intermediate reservoir empties directly into the conduct 19, or the cylindrical section 13b is connected with the conduct via a correspondingly restricted conical section 13a. Appropriate to that the plug 16 located inside of the intermediate reservoir 13 is adapted to such a formed intermediate reservoir 13 whereby preferably a sealing provided to the piston skirt and more preferably an O-formed flexible piston ring makes a safe use sure.

In all afore described embodiments the plug 10 arranged within the glass carpule 8 is also axially shifted in the direction of the arrow 51 as a result of the descending liquid level in the glass carpule 8. Hereby it is avoided that a vacuum is generated in the glass carpule or that a gas puffer is formed above the liquid level. In order to furthermore guarantee a complete emptying of the glass carpule 8, the front surface 10a (FIG. 9) of the plug 10 tapers, so that it contacts the shaft section of the glass carpule 8a (FIG. 9) when the liquid is completely descended.

Figure 10:
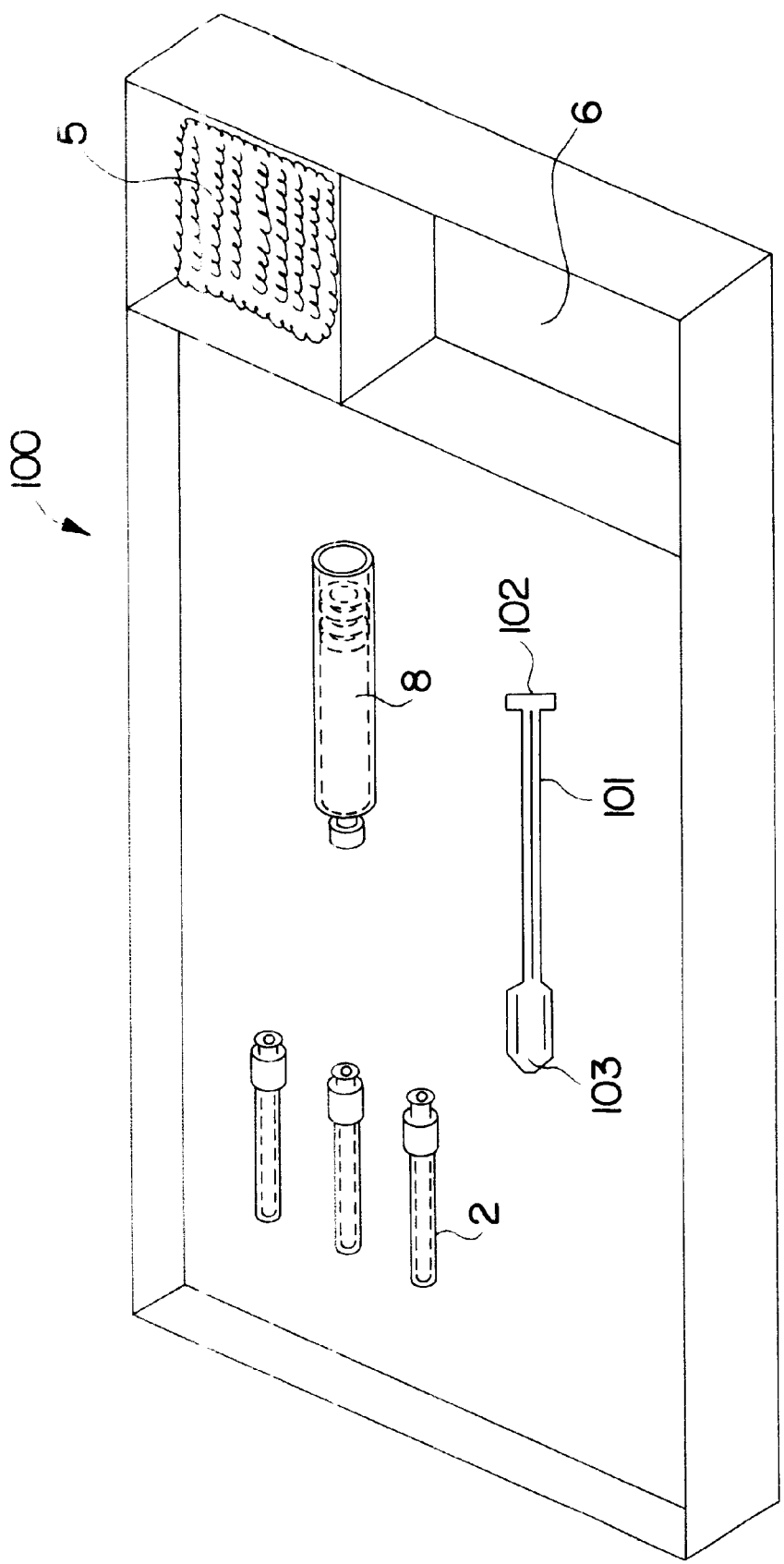
FIG. 10 is a perspective view of an embodiment of the refill unit.

In this state, the completely emptied glass carpule 8 can be removed from the device together with the detaching element 101 shown in FIG. 10. For this purpose, the detaching element comprises a grip section 102 for handling the detaching element 101 as well as a fixing section which can gear non-positively into a deepening 10b (FIG. 9) being provided in the plug 10 when the plug 10 is removed.

Moreover the refill unit shown in FIG. 10 comprises a multitude of cannulas 2 being provided with a corresponding cannula protector 45 (FIG. 3) for the sterile storing, a glass carpule designated with 8 serving as vessel being filled with the liquid pharmaceutical product. Moreover, the refill unit 100 comprises a number of sponges 5 moistened with an disinfectant, whereby the number of sponges 5 corresponds to the number of the cannulas 2. The refill unit 100 furthermore contains a section 6 taking up used cannulas, whereby, according to the embodiment shown in FIG. 10, this section can be closed by a cover which is not shown. This section 6 is collectively arranged at the refill unit 100 in a detachable way, so that, after taking up the used cannulas, this section 6 can be separately wasted, as far as this is legally prescribed or desired. The sale unit 1 usually comprises 10 cannulas 2, so that correspondingly the glass carpule 8 contains the liquid amount for 10 cannulas. Usually the liquid amount emitted each in single doses varies between 0.1 ml and 1 ml, so that correspondingly the glass carpule contains between 1 ml and 10 ml of the liquid pharmaceutical product. In order to avoid an evaporation of the disinfectant of the sponges 5, each sponge 5 is separately wrapped by a corresponding plastic foil in an air-tight way. The refill unit 100 taking up the afore described parts is collectively closed by a cover (not shown) or is arranged in the usual plastic wrapping, if necessary even in a sterile way. The afore described detaching element 101 is arranged in the refill unit 100.

The used term piercable membrane several times repeated means a flexible sealing disc being fixed at the carpule 8 by a flared flange, preferably by a metallic flared flange, as it is clearly shown in the drawings.

What is claimed is:

1. A device for emitting a given liquid amount of a pharmaceutical product in single doses, comprising:

a casing;

a vessel containing the pharmaceutical product receivable in a storage section located within said casing;

an intermediate reservoir;

said casing further including an outlet section from which the single dose of the pharmaceutical product is dispensed, the outlet section including a mounting section for detachably receiving a cannula in fixed engagement therewith, the cannula being communicative with said outlet section when received on said mounting section, the vessel being communicative with the outlet section via the intermediate reservoir such that when the vessel is received in the storage section, the given liquid amount of each single dose can firstly be drained from the vessel into the intermediate reservoir, and then from the intermediate reservoir into the outlet section, whereby the amount of the drained liquid can be determined for each single dose by the volume of the intermediate reservoir;

a protecting element disposed at said outlet section;

a first cylinder and a second cylinder surrounding the first cylinder arranged within the casing, the first cylinder and the second cylinder being shiftable axially relative to the casing, the storage section being disposed within the first cylinder and the intermediate reservoir being located within the second cylinder such that the first and the second cylinder are axially shiftable from a first position in which the cannula protrudes beyond the protecting element and in which the intermediate reservoir is emptied via a connecting conduct and the cannula communicative therewith, and a second position in which the cannula is shielded by the protecting element and in which the intermediate reservoir is filled with the single dose from the vessel received in the storage section.

2. The device according to claim 1, wherein the intermediate reservoir is filled with a single dose of the liquid pharmaceutical product by axially moving the first and the second cylinders relative to the casing from the first position into the second position.

3. The device according to claim 2, wherein the first and the second cylinders are each axially biased by a spring such that in the first position of the cylinders, the springs are released.

4. The device according to claim 3, wherein the spring of the second cylinder has a steeper characteristic spring line than the spring of the first cylinder.

5. The device according to claim 1, wherein both cylinders are fixed in the second position by a locking element.

6. The device according to claim 1, further comprising:

a piston disposed within the intermediate reservoir and axially shiftable in a direction of the outlet section.

7. The device according to claim 6, wherein:

an interior of the intermediate reservoir includes a cylindrically-shaped section and a conically-shaped end section adjacent the cylindrically-shaped section, the conically-shaped end section being directed to the outlet section and communicative therewith; and the piston is correspondingly configured to the interior of the intermediate reservoir.

8. The device according to claim 6, wherein the intermediate reservoir is filled with a single dose of the pharmaceutical product by an axial shifting of the piston in the direction of the vessel.

9. The device according to claim 8, wherein a vacuum is produced in the intermediate reservoir for the transport of a single dose of the liquid pharmaceutical product from the vessel into the intermediate reservoir by axially shifting the piston in the direction of the vessel.

10. The device according to claim 9, wherein the connecting conduct connects the intermediate reservoir with the outlet section, said device further comprising a closing element permitting said connecting conduct to be airtightened.

11. The device according to claim 10, wherein the closing element is provided as a detachable closing element located at an end of the conduct, the closing element including a sealing section for air-tightening an outlet of the conduct.

12. The device according to claim 10, wherein the closing element is fixed at the mounting section for fluid-tightening the connecting conduct directed to an outside of the outlet section.

13. The device according to claim 1, wherein the connecting conduct extends between the vessel when same is received in the storage section and the intermediate reservoir.

14. The device according to claim 13, wherein the connecting conduct comprises a reflux valve which inhibits backflow of liquid from the intermediate reservoir into the vessel.

15. The device according to claim 13, wherein the connecting conduct is connected with the cannula in a fluid-tight way when the cannula is received on the mounting section.

16. The device according to claim 1, further comprising:
   means provided at said outlet for selectively restricting flow therethrough when transfer of the contents of said vessel to said intermediate reservoir is effected, and for permitting flow therethrough when transfer of the contents of said intermediate reservoir to said outlet is effected.

17. The device according to claim 16, further comprising:
   a piston carried on said vessel and sealably insertable into said intermediate reservoir, whereby relative movement of said at least portions of said vessel and said intermediate reservoir apart from one another creates a vacuum in said intermediate reservoir.

18. The device according to claim 1, wherein said vessel and said intermediate reservoir are aligned approximately along a common longitudinal axis.

19. The device according to claim 1, wherein said vessel is a carpule receivable in a chamber formed in said housing.

20. The device according to claim 19, wherein said carpule includes a plug for sealing said carpule, said plug being movable in response to said transfer of the contents from said vessel to said intermediate reservoir.

21. The device according to claim 1, wherein the mounting section comprises the protecting element which covers at least a part of the cannula when fixed at the mounting section.

22. A device for emitting a given liquid amount of a pharmaceutical product in single doses, comprising:
   a casing;
   a vessel containing the pharmaceutical product receivable in a storage section located within said casing;
   an intermediate reservoir;
   said casing further including an outlet section for the single dose of the pharmaceutical product, the outlet section including a mounting section, the vessel being communicative with the outlet section via the intermediate reservoir such that when the vessel is received in the storage section, the given liquid amount of each single dose can firstly be drained from the vessel into the intermediate reservoir, and then from the intermediate reservoir into the outlet section, whereby the amount of the drained liquid can be determined for each single dose by the volume of the intermediate reservoir;
   a cannula detachably receivable in fixed engagement with the mounting section and communicative with the outlet section when received on said mounting section;
   a protecting element disposed at said outlet section; and
   a first cylinder and second cylinder surrounding the first cylinder and being arranged within the casing such that the first cylinder and the second cylinder are shiftable axially relative to the casing, the storage section being disposed within the first cylinder and the intermediate reservoir connected with the vessel is located within the second cylinder such that the first and the second cylinders are axially shiftable from a first position in which the cannula protrudes over the protecting element and in which the intermediate reservoir is emptied, into a second position in which the cannula is shielded by the protecting element, and such that for filling the intermediate reservoir, the first cylinder is axially shiftable into a third position in the direction of the vessel relative to the second position of the second cylinder.

23. The device according to claim 22, wherein:
   each of said first and second cylinders is biased by a spring, whereby a first spring pre-tensions the position of the first cylinder in the third position and a second spring pre-tensions the position of the second cylinder in the second position; and
   the first cylinder is fixable in the third position by a first locking element and the second cylinder is fixable in the second position by a second locking element.

24. The device according to claim 22, further comprising:
   a common release button, operation of which first releases the second locking element and then releases the first locking element with a corresponding time delay.

* * * * *